United States Patent [19]

Gamble

[11] Patent Number: 4,753,788
[45] Date of Patent: Jun. 28, 1988

[54] METHOD FOR PREPARING SMALL VESICLES USING MICROEMULSIFICATION

[75] Inventor: Ronald C. Gamble, Altadena, Calif.

[73] Assignee: Vestar Research Inc., Pasadena, Calif.

[21] Appl. No.: 696,727

[22] Filed: Jan. 31, 1985

[51] Int. Cl.$^4$ .................. A61K 43/00; A61K 49/00; B01J 13/02
[52] U.S. Cl. .................. 424/1.1; 264/4.1; 264/4.6; 424/420; 424/450; 436/829
[58] Field of Search ............ 264/4.1, 4.6; 424/1.1, 424/420, 450; 436/829

[56] References Cited

U.S. PATENT DOCUMENTS

| | | | |
|---|---|---|---|
| 4,016,100 | 4/1977 | Suzuki et al. | 427/3 X |
| 4,310,506 | 1/1982 | Baldeschwieler et al. | 264/4.1 X |
| 4,411,894 | 10/1983 | Schrank et al. | 514/78 X |
| 4,485,054 | 11/1984 | Mezei et al. | 436/829 X |
| 4,544,545 | 10/1985 | Ryan et al. | 424/1.1 |

OTHER PUBLICATIONS

Gregorladis: "The Carrier Potential of Liposomes in Biology and Medicine", The New England Journal of Medicine, vol. 295, No. 13, Sep. 23, 1976, pp. 704–710.

Primary Examiner—Richard D. Lovering
Attorney, Agent, or Firm—Lyon & Lyon

[57] ABSTRACT

A method is provided for preparing small (less than 2000 Å) lipid vesicles in commercial quantities by microemulsifying lipid compositions using very high shear forces generated in a homogenizing apparatus operated at high pressures at a selected temperature. These vesicles are suitable for various biological applications including targeting of tumors in a body for diagnosis and treatment.

22 Claims, 1 Drawing Sheet

METHOD FOR PREPARING SMALL VESICLES USING MICROEMULSIFICATION

FIELD OF THE INVENTION

This invention relates to a process for producing small lipid micellular particles in the form of unilamellar vesicles in commercial quantities by microemulsifying lipid compositions using very high shear forces.

BACKGROUND OF THE INVENTION

Unilamellar phospholipid micellular particles in the form of vesicles (also known as liposomes) have received increasing attention from researchers as carriers of various substances, such as imaging agents and for diagnosis of abnormalities such as tumors in humans using animal models. In particular, it has been shown that small vesicles (less than 2000 Å) may be labelled to target tumors (Proffitt, et al., *J. Nucl. Med.* 24(1), p. 45–50 (1983)) incorporated hereinafter by reference. Such vesicles are also useful as potential carriers of therapeutic agents for treatment of tumors. Alternatively, small vesicles are useful for in vitro immunoassays. U.S. Pat. No. 4,342,826 and D. Papahadjopoulos (Ed.) *Annals N.Y. Acad. Sci.*, 308 (1978). Additionally, the vesicles containing imaging or therapeutic agents may be modified by incorporating various carbohydrate derivatives into the vesicle surface to increase tissue specificity of the vesicles, or by adding cholesterol to increase the stability of the vesicles. Mauk and Gamble, *Anal. Bioc.* 94, pg. 302–307 (1979); Mauk, et al., *P.N.A.S. (U.S.A.)* 77(8), pg. 4430–4434 (1980); and *Liposome Technology, Targeted Drug Delivery and Biological Interaction*, Vol. III, G. Gregoriadis (Ed.), C.R.C. Press, Inc. (1984), all of which are incorporated herein by reference.

The prior art shows that vesicles such as liposomes may be produced using the methods of sonication, dialysis, injection or reverse phase evaporation. These procedures are well known and may be found in the following articles: Huang, *Biochemistry* 8, pg. 344 (1969) (Sonication); Rhoden and Goldin, *Biochemistry* 18, pg. 4173 (1979) (dialysis); and Kremer et al *Biochemistry* 16, pg. 3932–3935 (1977) (injection); and *Liposome Technology, Preparation of Liposomes*, Vol. I, 6 Gregoriadis (Ed.), CRC Press Inc. (1984), all of which are incorporated herein by reference. These methods share several disadvantages including the inability to conveniently produce commercial quantities of such vesicles.

The use of homogenizing devices to produce emulsions from solutions with soluble and insoluble components is well known in the art. U.S. Pat. No. 4,127,332. Several such homogenizing devices operate by creating shearing forces to disperse the insoluble and soluble components. These shearing forces result from the process known as cavitation which involves the rapid formation of bubbles within the sample solution as it passes through narrow channels causing a reduction in the vapor pressure of the fluid. The bubbles then collapse as the solution moves out from these channel areas, generating a shearing force. Such homogenizing devices, however, have been operated at relatively low pressures (usually below 10,000 psi) for the purpose of creating emulsions with large particles (greater than 1 micron) such as lipoproteins for baking purposes, (U.S. Pat. No. 4,360,537), or simply to form an emulsion of oil and water. U.S. Pat. No. 4,026,817.

Recently, various mechanical devices such as homogenizers have been employed in producing vesicles. U.S. Pat. No. 4,411,894. However, these devices have been used to assist with the initial dispersion of vesicle precursor substances such as soya or egg lecithin which do not require high shear forces to form vesicles and which do not form vesicles optimally stable in vivo. In addition, the French Press and Pressure Cell has been used to generate small vesicles. U.S. Pat. No. 4,263,428. A disadvantage of this device is that it requires extra time to reload a sample since it provides no means to recirculate the lipid solution through the device.

It is, therefore, an object of the present invention to provide an efficient, time-saving and reproducible process, having the advantages enumerated above for producing commercial quantities of small, unilamellar vesicles, especially vesicles suitable for treatment and diagnosis of tumors in a body.

SUMMARY OF THE INVENTION

The present invention comprises a process for the production of small (less than 2000 Å) unilamellar vesicles in commercial quantities wherein a solution containing lipids and other components capable of forming the desired vesicles is placed in a modified homogenizing apparatus, maintained at a selected temperature, and subjected therein to very high shearing forces, for a selected time.

The process of this invention further comprises a method for preparing small (less than 2000 Å) unilamellar lipid vesicles suitable for use as carriers of imaging agents for targeting tumor cells in a body. These vesicles are prepared by placing a solution of components capable of forming vesicles, an ionophore, a chelating agent and, in some applications, a radioactive tracer bound to said chelating agent, in a homogenizing apparatus and subjecting the solution to very high shearing forces while maintaining the solution at a selected temperature, for a selected time.

This invention also includes a method for preparing small (less than 2000 Å) unilamellar vesicles suitable for use as carriers of therapeutic agents for treating tumors in a body. These vesicles are obtained by placing a solution of components capable of forming vesicles, a therapeutic agent and, in some applications, an ionophore, a chelating agent and a radioactive tracer bound to said chelating agent, in a homogenizing apparatus and subjecting this solution to very high shearing forces while maintaining the solution at a selected temperature, for a selected time.

DESCRIPTION OF THE PREFERRED EMBODIMENT

The process of the present invention begins with the preparation of a solution of materials capable of forming vesicles. Preferably the lipids for use in the present invention are phospholipids and may include dipalmitoyl phosphatidylcholine (DPPC); distearoyl phosphatidylcholine (DSPC) or similar materials.

Amphiphilic molecules other than phospholipids such as phosphoglycerides may also be used. See generally, *The Hydrophobic Effect* by Charles Tanford, Wiley-Interscience, (1980), Biological Lipids, (Ch. 11) pg. 106–109 (incorporated herein by reference). It is preferable to use compounds with hydrocarbon chains which exhibit phase transitions at relatively high temperatures (greater than 37° C.) to form vesicles with improved stability in vivo. It is known that phase transition points are a function of hydrocarbon chain length. *The Hydrophobic Effect*, Charles Tanford, (2nd Ed. 1980). Thus, vesicle-forming compounds with carbon chains of at least 16 carbon atoms are preferable. However, it is more difficult to accomplish vesicle formation with such longer hydrocarbon chains.

I have surprisingly found that the use of a homogenizing apparatus operated at higher pressures then specified, and equipped with a reservoir capable of maintaining selected temperatures can convert such long-chain hydrocarbon compounds into improved vesicles which can thus be produced in commercial quantities.

Cholesterol may be incorporated into the lipid solution to increase the stability of the vesicles which are prepared using the process disclosed herein. In addition, if the vesicles are used to carry imaging agents for locating and diagnosing tumors, a chelating compound may be added to the lipid solution to become entrapped within the vesicles, as well as an ionophore for loading external cations for radiolabelling into the chelating agent within the vesicles. Imaging is accomplished using a gamma-camera. The preferred ionophore is A23187, but other useful ionophores are polyethers such lasalocid A(X-537A) and 5-Bromo derivatives of lasolocid; cyclic depsipeptides such as beauvericin; cyclic peptides such as valinomylin; and antifungal toxins such as arenaciolide. The chelating agent is preferably nitriloacetic acid (NTA), although other chelators may also be used. For example, where the cations are polyvalent metal ions, polyamino carboxylic acid chelators for such ions may be employed, such as ethylenediamine-tetracetic acid, diethylenetriamine-pentaacetic acid, diamino-cyclohexanetetra-acetic acid and iminodiacetic acid. Other agents useful for imaging tumors may include contrast agents for X-ray imaging such as diatrizoic salts, for example Hypaque meglumine, or Nuclear Magnetic Resonance (NMR) imaging agents such as paramagnetic ions and their complexes with strong chelating agents, for example, Gadolinium-DTPA.

This invention also contemplates the use of vesicles to carry therapeutic agents to treat abnormalities such as tumors in a patient. Chemotherapeutics such as methotrexate, arabinosyladenine or actinomycin D may be attached to the vesicles during the microencapsulation process of this invention. Alternatively, radionuclides such as Iodine 131, Yttrium 90 or Phosphorus 32 may be attached to the vesicles produced, using the methods disclosed herein, for radiotherapy of tumors.

This invention requires the use of a homogenizing apparatus capable of operation at high pressures to generate the very high localized shearing forces necessary to produce the microemulsion of small, unilamellar lipid vesicles from the solutions of vesicle-forming materials disclosed herein. Such an apparatus is a modified Gaulin Homogenizer (Model 15M) which accomplishes dispersion of the lipid solution by means of a homogenizing valve. The specification for the homogenizer prescribes a continuous operating pressure of 8,000 p.s.i., or an intermittent operating pressure of 10,000 p.s.i. I have found, however, that with proper safety precautions the homogenizer can operate for short periods of time for up to 12,000 p.s.i. of pressure. In the preferred embodiment, the homogenizer recirculates solution past the homogenizing valve at the rate of 1 liter per minute.

The Gaulin homogenizer is modified with two heat exchange reservoirs maintained at approximately 5°–10° C. and 80° C. and equipped with a feedback loop to assist in converting the longer chain hydrocarbon vesicle-forming components into vesicles. When higher temperatures are used in the heat exchange reservoir, a wider range of pressure settings may be used to generate vesicles of the desired size. Since the actual temperature of the lipid solution is several degrees higher in the homogenizing valve area where the shearing forces are generated, at the higher reservoir temperatures higher pressures may not be advisable because they may further increase the temperature of the solution in the dispersing valve area. The higher temperature of operation thus allows one to lower the pressure settings and still generate vesicles of suitable dimensions for various biological applications. As noted above, this effect is probably due to the increasing ease of converting larger chain hydrocarbon amphiphilic molecules into vesicles at temperatures above their phase transition points.

This invention also makes use of a Nicomp 200 Laser Particle Size Instrument which determines the distribution of particle sizes in a solution using the principles of dynamic light scattering. Briefly, laser light is passed through a vesicle sample solution and particle size is determined from the time behavior of fluctuations in the scattered light intensity using a series of time-dependent calculations expressed as an auto-correlation function. Particle hydro-dynamic radius (Rh) is calculated by the Stokes-Einstein relation using least squares analysis. The mean radius and variation of the particle distribution produced by the Nicomp from a sample is obtained by assuming that the distribution is Gaussian in shape. However, when there is a bimodal particle size distribution this assumption is not appropriate and the manufacturers of the Nicomp have provided proprietary instrument programs which enable the sample data to be assigned to a bimodal distribution to obtain the average mean diameter (a function of Rh) for the particles in such a distribution. A bimodal size distribution was obtained for vesicles prepared by the methods of the present invention. Using the data fitting program purchased from the Nicomp Manufacturers (Santa Barbara, CA), values for the average mean diameter (Stokes-Einstein (Rh×2)) of the vesicles in a sample were obtained. In addition, microscopic examination of vesicles in several samples run through the Nicomp Size Instrument revealed that the diameters of a majority of vesicles actually fell within the main peak of the bimodal size distribution curve obtained from the Nicomp. Thus, for the size data reported in the examples herein, the diameters of the vesicles in a given sample prepared by the methods of this invention are given as both the average Stokes-Einstein and the average main peak vesicle diameters.

For a more detailed explanation of dynamic light scattering, see B. Chu, *Laser Light Scattering*, Academic Press, N.Y. (1974), and see instructional materials accompanying the Nicomp Size Instrument.

BRIEF DESCRIPTION OF THE DRAWINGS

The following examples are presented solely to illustrate the invention, and are not intended to be limiting in any way. In the examples, reference is made to FIGS. 1, 2 and 3 of the drawings and Tables I–III.

EXAMPLE I

Preparation of Vesicle Solution

Vesicle solutions were prepared using the techniques described by Mauk et al., *Anal Bioc.* 94 pg. 302-307 (1979), and disclosed in U.S. Pat. No. 4,310,506, both incorporated herein by reference. Briefly, L-α-distearoyl phosphatidylcholine (DSPC) from Calbiochem, was used as the phospholipid component of the vesicle solution without further purification. Cholesterol (CH) was purchased from Sigma, and the trisodium salt of nitriloacetic acid (NTA) from Aldrich Chemical Co. The ionophore, A23187 was obtained from Eli Lilly and Co.; its preparation is described in U.S. Pat. No. 3,960,667 which is incorporated herein by reference.

For this Example, DSPC and cholesterol were used in a mole ratio of 2:1 (5 gm total lipid, DSPC and CH), and dissolved in 50 ml of chloroform, then dried to a film in a rotary evaporator. The film was dried under vacuum overnight and rehydrated with 0.5 liter phosphate buffered saline ($P_i$/NaCl: 0.9% NaCl/5 mM sodium phosphate at a pH of 7.4). The concentration of total lipid was approximately 10 mg/ml total lipid.

Figure 1:
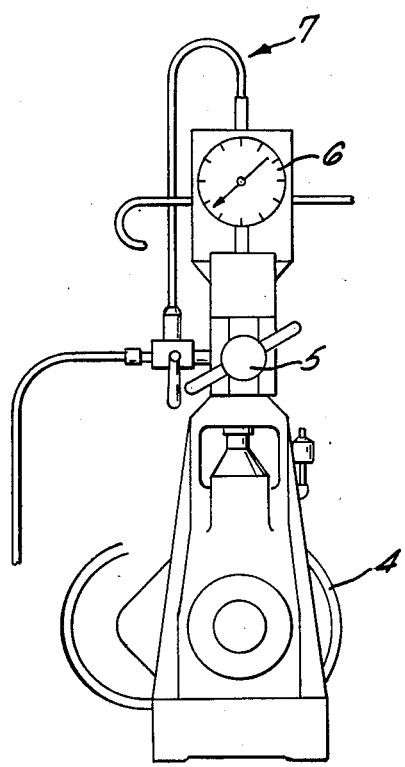
FIG. 1 is a front view of a modified Gaulin homogenizing apparatus.
Figure 2:
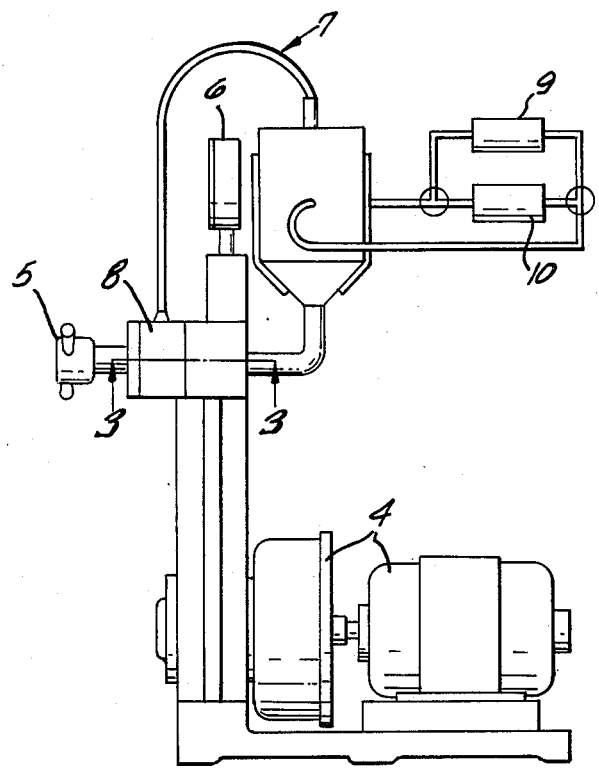
FIG. 2 is a side view of a modified Gaulin homogenizing apparatus.

A modified Gaulin Homogenizer, Model 15M, as shown in FIGS. 1 and 2 was used to carry out microemulsification of the lipid solution. The homogenizer consists of a transmission, 4, a pressure adjusting screw, 5, a pressure gauge, 6, a recirculation loop 7, and a homogenizing valve assembly, 8. The modification consists of two heat exchange reservoirs, 9 and 10 in FIG. 2 which maintain the lipid solution at a selected temperature in the range of 40°-80° C., depending on the pressure at which the sample will be run, but preferably between 70°-75° C. One reservoir, 9 of FIG. 2 is kept in the range of approximately 5°-10° C., the other reservoir, of FIG. 2 is kept at approximately 80° C.

Figure 3:
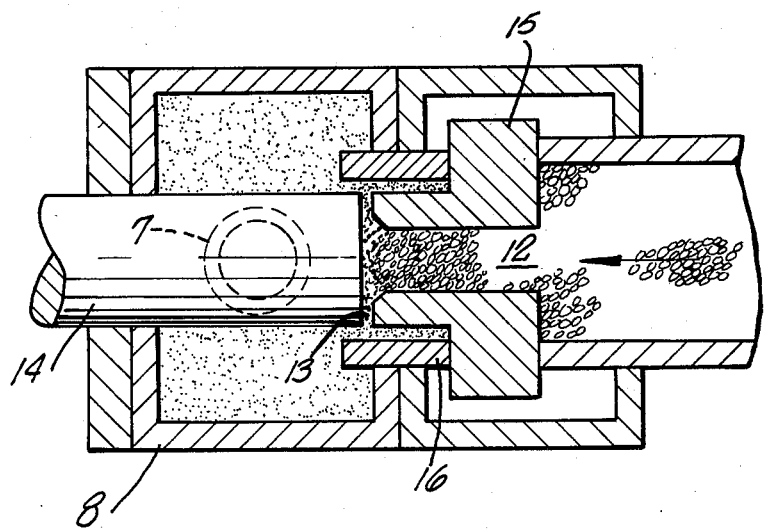
FIG. 3 is a cross-section of the homogenizing valve assembly taken along line 3—3 of FIG. 2.

In operation the lipid solution prepared as above is placed in the solution receptacle, 11 of FIG. 1, and is then moved into the valve area 12 of FIG. 3 at high pressure and low velocity. Vapor bubbles form in the solution as a result of the rapid increase in velocity accompanied by a decrease in pressure as the solution moves through the channel 13 between the valve 14 and valve seat 15. The vapor bubbles then implode as the solution exits the valve area 12 at a lowered velocity and at an increased pressure. This process of bubble formation and implosion (also known as cavitation) generates the high shearing forces which microemulsify the lipid solution. The microemulsion then exits the valve area 12, impinges on the impact ring 16 and recirculates through the homogenizer.

It is preferable that the homogenizing apparatus is operated for a time sufficient to allow a number of circulations of the entire lipid solution through the homogenizing valve area (6 of FIG. 3) to achieve optimal micromulsification. Taking into consideration the volume (0.5 liter) and flow rate (one liter/min.) of the modified Gaulin homogenizing apparatus used in this Example, at least 20 circulations (corresponding to approximately 10 minutes) but not greater than 200 circulations (100 minutes) were found to be sufficient to produce a micro-emulsion of small vesicles suitable for biological applications.

In this Example, vesicle compositions were run through the homogenizer at temperatures selected in the range of approximately 50°-80° C. for time periods ranging from 15-90 minutes. The pressure for each run varied between approximately 8,000 psi to 12,000 psi.

After each run, the size of the vesicles in the microemulsion was determined.

VESICLE SIZING

Approximately 1 milliliter of the homogenized vesicle suspension was centrifuged at 15,000 rpm for 10 minutes using an Eppendorf Microcentrifuge Model 5414. Large particles which would cause error in the light scattering measurement are pulled to the bottom while the vesicles remain suspended. A 6×50 mm test tube was rinsed with filtered PBS then filled to within 5 mm of the top with PBS. 3-4 ul of the centrifuged vesicles were then placed in the test tube and the contents mixed by inverting the tube several times. A Nicomp 200 Laser Particle Sizer Instrument was used to determine the average mean diameter and main peak diameter as described above for a sample of vesicles. Use of the Nicomp Particle Sizer is described in the instruction manual. The temperature was set at 20° C. An appropriate channel width (preferably 1.4E1 m sec) and prescale factor (preferably 1) were selected. The sample was then run through the Nicomp. After 50,000 counts a reasonable estimate of particle size was obtained.

Table I shows vesicle size data summarized for vesicles prepared by the micromulsification procedures described in this example at different pressures for different time periods and at reservoir temperatures ranging from approximately 50°-80° C.

TABLE I

| TEMP (°C.) | PRESSURE (PSI) | SIZE (Å) *AVERAGE MAIN PEAK DIAMETER OF VESICLES | AVERAGE STOKES-EINSTEIN DIAMETER | HOMOGENIZING TIME (MIN) |
|---|---|---|---|---|
| 50-55 | 11000 | 670 | 1020 | 15 |
| 50-55 | 11000 | 610 | 990 | 30 |
| 50-55 | 11000 | 570 | 1000 | 60 |
| 50-55 | 11000 | 578 | 1060 | 75 |
| 50-55 | 11000 | 560 | 1110 | 90 |
| 50-55 | 12000 | 590 | 970 | 15 |
| 50-55 | 12000 | 550 | 940 | 30 |
| 50-55 | 12000 | 510 | 900 | 60 |
| 50-55 | 12000 | 470 | 870 | 75 |
| 70-75 | 11000 | 630 | 1220 | 15 |
| 70-75 | 11000 | 570 | 1160 | 30 |
| 70-75 | 11000 | 520 | 1070 | 60 |
| 70-75 | 11000 | 500 | 830 | 75 |
| 70-75 | 11000 | 510 | 880 | 90 |
| 70-75 | 8000 | 570 | 1030 | 15 |
| 70-75 | 8000 | 590 | 1000 | 30 |
| 70-75 | 8000 | 540 | 890 | 60 |
| 70-75 | 8000 | 520 | 880 | 75 |
| 70-75 | 8000 | 520 | 840 | 90 |

The data in Table I shows that small lipid vesicles (less than 2000 Å) are obtained by microemulsification using high shear forces generated in a homogenizer operated at high pressure.

At the lower reservoir temperature (approximately 50°-55° C.) small vesicles are reproducibly generated at higher pressures (greater than 10,000 psi). Vesicles are preferably obtained by microemulsification at the higher reservoir temperatures (approximately 70°-75° C.) which generate suitable small vesicles at pressures greater than 8,000 psi. This high temperature effect thus allows a greater range of pressures to be used which may be a function of the difficulty of converting longer-chain hydrocarbons into vesicles due to higher phase transition points. A reduced temperature necessitates operation of the homogenizing apparatus at higher pressures to generate sufficient shearing forces to convert such vesicle precursors into vesicles.

Such vesicles are useful for various biological applications, such as diagnosis and treatment of tumors and in vitro assays.

EXAMPLE II

Preparation of Vesicles Modified for Imaging Tumors

Vesicle solutions were prepared as in Example I with the following modifications: the ionophore A23187 was added to the DSPC:CH mixture, to yield a mole ratio for DSPC, CH, A23187 of 2:1:0.004 (5 gm total lipid, DSPC and CH) using the procedures disclosed in U.S. Pat. Nos. 4,310,506, 3,960,667 and in Mauk et al., *P.N.A.S.* U.S.A., 76, (2) 765-769 (1979), all of which are incorporated herein by reference. A23187 permits loading of lipid vesicles with a radiolabelling cation such as $^{111}In^{+3}$. The inclusion of small amounts of A23187 does not interfere with the formation of unilamellar vesicles by the microemulsification procedure.

The DSPC, CH and A23187 components were dissolved in 50 ml chloroform and dried to a thin lipid film as above. The dried lipid film was then rehydrated with a 0.5 liter PBS solution containing the weak chelator NTA (1 mM), at pH 7.4. The concentration of total lipid was approximately 25 mg/ml. As disclosed in U.S. Pat. No. 4,310,506 and Mauk, et al., *P.N.A.S.* USA 76 (2), pg. 765-769 (1979), NTA provides the driving force for the net transfer of cations for radiolabelling into the vesicles. While NTA is the preferred chelator as mentioned above, other chelators may be used. In addition, while $^{111}In^{+3}$ is the preferred cation for radiolabelling vesicles for biodistribution studies and diagnostic procedures, any cation which can be bound to a chelating agent may be used. The cations are preferably selected from the group of radioactive tracers, for example $^{111}In$, $^{45}Ca$, $^{51}Cr$, $^{99}Tc$, $^{67}Ga$, $^{57}Co$ and $^{65}Zn$.

After rehydration with the NTA in PBS, the mixture was microemulsified in a modified Gaulin Homogenizer, as described in Example I. A range of time periods and pressure settings were used as described in Example I. The preferred parameters for producing small vesicles suitable for the biodistributions of this example were found to be microemulsification for 60 minutes at 10,000 p.s.i. with a solution temperature of 70° C.

The microemulsion obtained was then filtered by standard gel filtration techniques to separate larger particulate matter and excess (unencapsulated) NTA from the small vesicles encapsulating NTA. The small vesicles were then concentrated using an Amicon Hollow-Fiber concentrator apparatus, and the total lipid concentration determined using a phosphate assay. PBS was then used to dilute the vesicles to a final total lipid concentration of 25 mg/ml.

LOADING

Vesicles were then loaded with $^{111}In^{+3}$ using the procedures described by Mauk and Gamble, *Anal. Bioc.* 94, pg. 302-307 (1979). Briefly, 500 μL (5 mg lipid) of vesicles were incubated with 35 μl of 3.4 μM InCl₃ in 104 mM sodium citrate, (pH 7.4) and 1-50 μl of $^{111}In^{+3}$ depending on the required activity. A volume of 2×PBS equal to that of the $^{111}In^{+3}$ addition was included in the incubation mixture. Maximal loading was accomplished by incubating at 80° C.

The vesicles were analyzed to determine suitability for biodistribution and targeting studies as compared with vesicles obtained by sonication. Sonicated vesicles were prepared as described by Mauk and Gamble, *Anal. Bioc.* 94, pg 302-307 (1979) and U.S. Pat. No. 4,310,506, both of which are incorporated herein by reference. Briefly, a lipid solution of the same composition as discussed above for Example I was dried then rehydrated with 0.5 ml of 1 millimolar NTA in PBS. The mixture was sonicated in a water bath at room temperature for 10 minutes, the incubated at 60° C. for 10 minutes to anneal any structural defects. The vesicles were then centrifuged at low speed to remove titanium and any highly aggregated materials. The NTA that did not incorporate was removed by passing the preparation over a Sephadex G-50 column equilibrated with PBS. The vesicles were then characterized as described below.

VESICLE SIZING

Sizing of the vesicles produced by the methods of this Example was accomplished as described for Example I using the Nicomp Sizing Instrument and was compared to results obtained in producing sonicated vesicles. As shown in TABLE II the methods of this invention yield vesicles with sizes in the range of 400 Å-1000 Å comparable to sizes of sonicated vesicles, and found by the inventor to be suitable for use in biodistribution and targeting studies.

TABLE II

Characteristics of Microemulsified Vesicles vs. Sonicated Vesicles

| | SIZE (Å) | | $^{111}In^{+3}$ |
|---|---|---|---|
| | Stokes-Einstein Diameter (Rh × 2) | Main Peak Diameter | Loading Efficiency |
| 1. Microemulsified | 870 | 660 | 80.1% |
| 2. Sonicated | 830 | 510 | 83.1% |

LOADING EFFICIENCY

The efficiency of loading the $^{111}In^{+3}$ into vesicles was determined as follows: 100 μL of $^{111}In^{+3}$ vesicle preparation loaded as described above was added to 0.5 grams of moistened Chelex (Dow Chemical Corp.) previously adjusted to pH 7.4 and mixed for two minutes. 900 μL of PBS was added, and the mixture was centrifuged in a tabletop centrifuge for 5 minutes at room temperature. 500 μL of supernatant was removed and the loading efficiency (percentage of vesicles loaded) was determined by counting in a Gamma counter the radioactivity of the 500 μL sample divided by the radioactivity of the 100 μL of original vesicle preparation and multiplying by 200.

As indicated in Table II, the efficiency of loading the cation $^{111}In^{+3}$ into the vesicles produced by microemulsification was found to be greater than 80%, which is comparable to values previously obtained for $^{111}In^{+3}$-loaded vesicles prepared by sonication. Mauk and Gamble, *Anal. Bioc.* 94, pg. 302-307 (1979).

BIODISTRIBUTION

To explore the suitability of the vesicles obtained in this example for use in vivo, vesicles containing the radioactive tracer $^{111}In^{+3}$ were administered to BALB/C female mice which were previously implanted subcutaneously in the right thigh with EMT 6 tumors 9-10 days prior to the initiation of these experiments to permit analysis of the biodistribution of the vesicles in animal tissue.

Intravenous injection was made via a lateral tail vein. Each mouse was then weighed and housed for 24 hours. Prior to sacrificing, the mice were anesthetized with ether and approximately ½ to 1 milliliter of blood was removed via the orbit and placed into a Beckman Gamma Counter 5500 gamma counting tube. The mice were then sacrificed by cervical dislocation and the following samples dissected: tumor, lung, liver, spleen, kidney, muscle, intestine, stomach, skin, tail and carcass. These samples (excluding muscle, intestine, stomach, skin, tail and carcass), were thoroughly rinsed in PBS and placed in gamma counting tubes and weighed. All samples were counted in the gamma counter for 1 minute to calculate the percentage of injected dose (radioactivity) per gram for each tissue. Two standards of vesicles were counted along with the tissue samples.

The results of biodistribution of radiolabelled vesicles prepared by microemulsification at 10,000 psi (at temperatures of about 70°-75° C.) are summarized in TABLE III. Table III also compares these results with data obtained for the biodistribution of vesicles prepared by sonication and labelled with $^{111}In^{+3}$.

TABLE III

BIOLOGICAL DISTRIBUTION OF VESICLES
Average % Injected dose/gm Tissue for 5 mice

| TISSUE | MICROEMULSIFIED VESICLES | SONICATED VESICLES |
|---|---|---|
| 1. Blood | 8.1 | 10.4 |
| 2. Tumor | 34.0 | 34.0 |
| 3. Lung | 5.3 | 6.2 |
| 4. Liver | 19.8 | 18.4 |
| 5. Spleen | 26.2 | 25.1 |
| 6. Kidney | 10.6 | 9.2 |
| 7. Muscle | 1.2* | 0.8 |
| 8. Intestine | 4.1 | 3.1 |
| 9. Stomach | 2.3 | 2.5 |
| 10. Skin | 3.3 | 3.7 |
| 11. Tail | 2.6 | 2.0 |
| 12. Carcass 1-3 | 1.7 | 1.5 |

Tissue distributions were thus found to be comparable for the microemulsified and sonicated vesicles.

These results demonstrate that vesicles produced by the microemulsion process disclosed herein possess attributes of size and stability comparable to vesicles produced by sonication, and are suitable for use in vivo to target tumors for diagnosis and treatment, as well as for other biological applications such as in vitro bioassays.

Although this specification has been disclosed and illustrated with reference to particular applications, the principles involved are susceptible of numerous other applications which will be apparent to persons skilled in the art. The invention is, therefore, to be limited only as indicated by the scope of the appended claims.

What is claimed is:

1. A process for the preparation of small, unilamellar vesicles of less than 2000 Å suitable for biological applications comprising:
    (a) hydrating amphilillic molecules selected from the group consisting of phospholipids and phosphoglycerides having hydrocarbon chains of at least 16 carbon atoms, and other components capable of forming lipid vesicles that are stable in vivo;
    (b) dispersing said hydrated lipid in a homogenizing apparatus at a pressure within the range of approximately 8000 to approximately 13,000 psi and at a selected temperature maintained in the range of approximately 50° C. to 80° C. for time periods ranging from 15 to 90 minutes to generate a microemulsion containing small unilamellar lipid vesicles of less than 2000 Å; and
    (c) separating said small, unilamellar vesicles from unencapsulated materials.

2. The process according to claim 1 wherein said amphiphilic molecules are phospholipids selected from the group consisting of phosphatidylcholine, phosphatidylethanolamine and phosphatidylserine.

3. The process according to claim 1 wherein the amphiphilic molecules are selected from the group consisting of distearoyl phosphatidylcholine and dipalmitoyl phosphatidylcholine.

4. The process as defined in claim 1 wherein said step of dispersing is performed by operating said homogenizing apparatus at pressures in the range of approximately 8000 to 10,000 psi and at a reservoir temperature in the range of approximately 70°-75° C. for 60 minutes.

5. The process as defined in claim 1 wherein said step of dispersing is performed by operating the homogenizing apparatus at pressures in the range of approximately 10,000 to 12,000 psi and at a reservoir temperature in the range of approximately 50°-55° C. for 60 minutes.

6. The process according to claim 1 wherein said step of hydrating amphiphilic molecules capable of forming lipid vesicles includes the steps of:
    (a) dissolving said amphiphilic molecules and other components capable of forming lipid vesicles in an organic solvent solution;
    (b) drying said solution to a lipid film; and
    (c) rehydrating the dried lipid film.

7. The process as defined by claim 6 wherein said organic solvent is selected from the group consisting of ethers, chloroform and alcohol.

8. The process according to claim 1 wherein the amphiphilic molecules and other components capable of forming lipid vesicles are phospholipid and cholesterol in the mole ratio of 2 to 1.

9. The process as defined in claim 1 wherein the composition of vesicles comprises phospholipid, cholesterol and a therapeutic agent said therapeutic agent being contained in the solution used to hydrate the amphiphillic molecules.

10. The process as defined in claim 9 where said therapeutic agent is a chemotherapeutic agent.

11. The process according to claim 10 wherein said chemotherapeutic agent is selected from the group of antibiotics consisting of Daunomycin, Bleomycin, Adriamycin, Actinomycin D, Mytomycin C and Mithramycin.

12. The process according to claim 10 wherein said chemoratherapeutic agent is selected from the group of alkylating agents consisting of chlorambucil, cyclophosphamide and Triethylenemelamine.

13. The process according to claim 10 wherein said chemotherapeutic agent is selected from the group of antimetabolites consisting of methotrexate, 5-Fluorouracil, 6-Mercaptopurine and Arabinosylcytosine.

14. The process according to claim 9 whereinsaid therapeutic agent is a radiotherapeutic agent.

15. The process according to claim 14 wherein said radiotherapeutic agent is selected from the group consisting of the radionuclides Iodine 131, Yttrium 90 and Phosphorus 32.

16. A process for the preparation of small unilamellar vesicles of less than 2000 Å suitable for use in targeting tumors in a body for location and diagnosis of the tumors comprising the steps of:
 (a) dissolving amphiphilic molecules selected from the group consisting of phospholipids and phosphoglycerides having hydrocarbon chains of at least 16 carbon atoms, and other components capable of forming lipid vesicles that are stable in vivo in an organic solvent solution;
 (b) drying said solution to a lipid film;
 (c) rehydrating the dried lipid film with phosphate buffered saline containing a weak chelating agent;
 (d) dispersing said rehydrated lipid in a homogenizing apparatus at a pressure within the range of approximately 8000 to approximately 13,000 psi and at a selected temperature maintained in the range of approximately 50° to 80° C. for time periods ranging from 15 to 90 minutes to generate a microemulsion containing small unilamellar lipid vesicles of less than 2000 Å with an ionophore incorporated into the lipid bilayer and said vesicles containing the chelating agent;
 (e) separating said small unilamellar vesicles from unencapsulated vesicle precursor materials; and
 (f) loading said vesicles with radioactive cation for detecting the location of said vesicles when administered into a body.

17. The process according to claim 16 wherein said amphiphilic molecules are phospholipids and said other components capable of forming vesicles are cholesterol and an ionophore.

18. The process as defined in claim 17 wherein the phospholipid is selected from a group consisting of distearoyl phosphatidylcholine and dipalmitoyl phosphatidylcholine.

19. The process according to claim 17 wherein the ionophore is A23187.

20. The process according to claim 17 wherein the composition of the vesicles comprises phospholipid, cholesterol and ionophore in the mole ratio 2:1:0.004.

21. The process as defined in claim 16 wherein the chelating agent is nitriloacetic acid.

22. The process according to claim 16 wherein the radioactive cation is $^{111}In^{+3}$.

* * * * *